US005360606A

United States Patent [19]

Parke et al.

[11] Patent Number: 5,360,606
[45] Date of Patent: * Nov. 1, 1994

[54] BIOLOGICAL INOCULANT EFFECTIVE AGAINST ALTERNARIA

[75] Inventors: Jennifer L. Parke; Ann E. Joy, both of Madison, Wis.

[73] Assignee: Wisconsin Alumni Research Foundation, Madison, Wis.

[ * ] Notice: The portion of the term of this patent subsequent to Sep. 14, 2010 has been disclaimed.

[21] Appl. No.: 26,798

[22] Filed: Mar. 5, 1993

Related U.S. Application Data

[63] Continuation-in-part of Ser. No. 989,931, Dec. 10, 1992, Pat. No. 5,244,658, which is a continuation of Ser. No. 861,991, Feb. 18, 1992, abandoned, which is a continuation of Ser. No. 387,919, Jul. 31, 1989, abandoned, which is a continuation-in-part of Ser. No. 227,810, Aug. 3, 1988, abandoned.

[51] Int. Cl.[5] .............................................. C12N 1/20

[52] U.S. Cl. ................................ 424/93.47; 424/520; 424/195.1; 435/253.3; 435/874

[58] Field of Search .................. 424/93 N, 520, 195.1; 435/253.3, 874

[56] References Cited

U.S. PATENT DOCUMENTS

| | | | |
|---|---|---|---|
| 4,988,586 | 1/1991 | Toyoda et al. | 424/93 N |
| 5,244,658 | 9/1993 | Parke | 504/117 |

OTHER PUBLICATIONS

Hebbar et al., Plant Soil 133(1): 131-140 (1991) Abstract BA:92(2) 21503.

Kirinuki et al., J. Pestic. Sci (Nihon Noyaku Gakkaishi) 9(4):601-610 (1984) Abstract BA 79(7): 62272.

Hasegawa et al., Bull Coll Agric Vet Med Nihon Univ. 0(47): 224-232 (1990) Abstract 90(5): 55050.

Susuri et al., Plant Dis 66(4): 328-330 (1982) Abstract 74(5): 34849.

*Primary Examiner*—Douglas W. Robinson
*Assistant Examiner*—Jean C. Witz
*Attorney, Agent, or Firm*—Quarles & Brady

[57] ABSTRACT

Alternaria disease on plant leaves and stems is controlled by inoculating the plants with an effective amount of a biologically pure culture of a *Pseudomonas cepacia* strain. *Ps. cepacia* strain AMMD is a particularly effective biocontrol agent which inhibits leaf and stem blight caused by *Alternaria panax* in ginseng plants.

7 Claims, 1 Drawing Sheet

BIOLOGICAL INOCULANT EFFECTIVE AGAINST ALTERNARIA

CROSS-REFERENCE TO RELATED APPLICATION

This application is a continuation-in-part of copending application Ser. No. 07/989,931 filed Dec. 10, 1992, now U.S. Pat. No. 5,244,658, which was a continuation of application Ser. No. 07/861,991 filed Feb. 18, 1992, abandoned, which was a continuation of application Ser. No. 07/387,919 filed Jul. 31, 1989, abandoned, which was a continuation-in-part of application Ser. No. 07/227,810 filed Aug. 3, 1988, abandoned.

FIELD OF THE INVENTION

The present invention is generally directed to inoculants for plants, and particularly directed to a biological inoculant effective in controlling leaf and stem blight of plants, caused by the foliar pathogen Alternaria.

BACKGROUND OF THE INVENTION

Farm crops are continually plagued by a variety of pests which can stunt or damage crop growth or even completely destroy the crop. Some of the pests are in the form of weeds which grow similarly to the desired plant and compete for the nutrients provided by soil and water. Other pests are in the form of pathogens such as fungi and bacteria which are found in association with many plants.

One of the more serious problems associated with fungal pathogens in plants is root rot. For example, pea root rot caused by the fungus *Aphanomyces euteiches* is a serious problem in pea-growing areas, particularly in Wisconsin and other Great Lake states. The Aphanomyces fungus infects not only peas, but also snap beans and alfalfa, accounting for 10 to 15% losses in yield. In extreme cases, some fields, where the fungus population has been built up over the period of several years, have become essentially useless for these crops. Despite efforts to develop fungicides and commercially acceptable pea cultivars with resistance to this pathogen, there is presently no commercially available product capable of controlling Aphanomyces. Currently, the best way to avoid the disease loss is to avoid planting susceptible crops in soils with a high population of the Aphanomyces fungus. Unfortunately, the fungus can survive for many years in field soil and a long rotational time to other crops is not practical. As a result, there is a need to find an alternative disease control strategy to eliminate root rot caused by Aphanomyces and possibly other fungi.

A second serious problem of fungal pathogens is blight, such as the leaf and stem blight of American and Chinese ginseng caused by the *Alternaria panax* fungus. The ginseng plant is a perennial grown from seed which takes at least 3 to 4 years to reach marketable size. Between growing seasons, the ginseng plants are covered with straw mulch on which Alternaria spores can survive. Although *A. panax*-induced leaf and stem blight typically does not kill the entire ginseng plant, it can lead to reduced ginseng root growth. To minimize Alternaria damage, ginseng growers currently treat their crops with an EBDC fungicide (mancozeb). Unfortunately, the fungicide breakdown products are highly carcinogenic and use of the fungicide is slated for elimination. At present, ginseng growers must obtain permission annually to use the fungicide. Yet, its use is necessary since it has been estimated that 80% to 100% of all ginseng plants would suffer Alternaria blight without effective fungal control.

Related Alternaria species similarly affect other plants, such as crucifers, potatoes, and tomatoes, and cause similar problems for commercial growers. In particular, early blight of potatoes caused by *A. solani* is an extremely serious problem for potato growers in humid climates. Likewise, in regions that grow plants for oils, such as rapeseed and canola, *A. brassicae* and *A. brassicicola* endemic.

There is increasing interest in the use of living organisms to control such root and foliar diseases. Microscopic organisms are present in soil in populations of approximately 1 billion per cubic inch of soil. Some of the microorganisms cause disease and some are beneficial. The beneficial microorganisms are of major interest. It has long been known in agriculture that certain of these microbial inoculants can be used to facilitate the growth of certain plant species or to assist the plants in suppressing particular pathogenic organisms. For example, it has been a common practice to inoculate soybeans and other legumes at planting with bacterial cultures of the genus Rhizobium so that nitrogen-fixing nodules will form as a result of the plant-bacterium symbiosis.

Reference is now made to U.S. Pat. No. 4,588,584 to Lumsden, et al. which discloses a particular species of *Pseudomonas cepacia* which is effective in controlling Pythium diseases of cucumber and peas. The term "biocontrol agent", as used herein, refers to a living organism which controls diseases.

SUMMARY OF THE INVENTION

It is therefore an object of the invention to provide a biocontrol agent which is effective in biologically controlling foliar diseases in plants in the field.

It is also an object of the present invention to provide a biocontrol agent which is effective in reducing plant mortality caused by foliar pathogens.

It is further an object of the present invention to provide a process for increasing the crop yield in areas where Alternaria diseases are a problem.

These and other objects are met by the present invention which is directed to a process for controlling Alternaria fungal diseases by inoculating the plants with an effective amount of an essentially biologically pure culture of a Pseudomonas cepacia strain to control Alternaria disease.

The inoculum which controls Alternaria spore germination is also disclosed in this invention. As used herein, the term "inoculum" means a biological control agent which is introduced onto a host substance or into soil. The inoculum comprises an essentially biologically pure culture of a strain of the bacteria mentioned in the previous paragraphs.

The *Ps. cepacia* bacterial strains, and the process of their use on ginseng disclosed in the present invention, represent a significant advance in controlling Alternaria. Because the bacterial strains used are biologically pure cultures of a natural biological organism, massive quantities of the inoculum can be applied to the Alternaria-infested area with little danger of environmental contamination. In view of public concern for ground water contamination and aerial pollution from pesticides, the form of control disclosed in the present invention is an attractive and economic alternative to chemical pesticides and other methods of control.

Other objects, advantages and features of the present invention will become apparent from the following specification when taken in conjunction with the accompanying drawings.

DETAILED DESCRIPTION OF THE INVENTION

Figure 1:
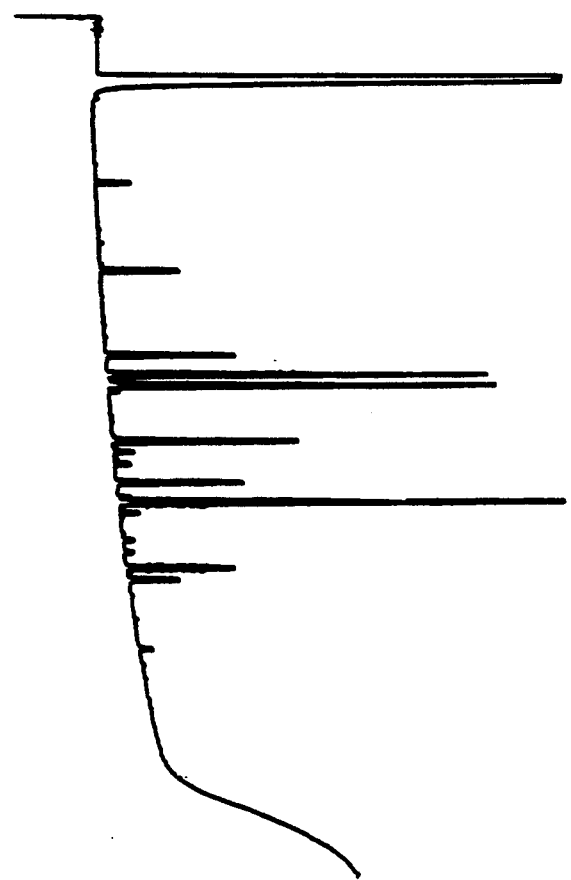
FIG. 1 is a graph illustrating the results of the mass spectrometric analysis of the fatty acid profile of *Pseudomonas cepacia* AMMD.

The present invention is directed to improving the growth and survival rate of plant crops, particularly ginseng plants, infested with the foliar fungus *Alternaria*, particularly the strain *Alternaria panax*, by inoculating the field crop with a biologically pure bacterial inoculant of a *Pseudomonas cepacia* strain such as AMMA, AMMD or ATCC 29424.

The AMMA and AMMD bacterial strains were initially isolated by one of the inventors of the present invention from over 200 strains of bacteria associated with pea plants in the field. *Pseudomonas cepacia* AMMD was initially isolated from the rhizosphere of healthy appearing pea plants grown in containment in soil known to be infested with the Aphanomyces fungus from the University of Wisconsin-Arlington Experimental Farm. To enable others to obtain a culture of strain AMMD, a sample has been deposited with the American Type Culture Collection (ATCC), and is identified at ATCC Accession Number 53795 deposited on Jul. 7, 1988. Strain AMMA was also deposited in the ATCC on the same date and was accorded ATCC Accession Number 53796. ATCC 29424 is a biologically pure culture of a *Pseudomonas cepacia* bacterium deposited at, and obtained from, the American Type Culture Collection of Rockville, Md.

The AMMA and AMMD bacterial strains were collected in the following manner. The root system from the pea plants was removed and agitated to shake off the excess soil. The hypocotyl and epicotyl segments of the roots were placed in distilled water, and sonicated. Thereafter isolations were made in a plate dilution process, known to the art, on a TSAC (tryptic soy agar cyclohexamide) medium. Cyclohexamide is an anti-fungal agent. Colonies were thereafter selected and screened according to methods 35 known to the art. The bacterial strains were thereafter stored in a DMSO solution at approximately −80° C. until required for use.

It has been found that the *Pseudomonas cepacia* bacterial strains may be mass produced in culture with relative ease. The strains are cultured in a suitable culture medium such as a commercially available nutrient broth yeast (NBY) extract. As the bacterial strains grow and multiply, essentially biologically pure cultures of the strain are formed which may be collected. The term "biologically pure culture" is used herein to refer to cultures of bacteria that have essentially no concentration of other strains of bacteria.

The approximately 200 bacteria strains were then screened for biocontrol activity in soil which has been naturally infested or artificially infested with the Aphanomyces fungus in order to determine which bacterial strains are effective biocontrol agents.

It is herein disclosed that in addition to protecting against fungal root diseases *Pseudomonas cepacia* strains AMMA, AMMD, also inhibit spore germination of Alternaria species such as *A. panax, A. brassicicola,* and *A. solani* as does strain ATCC 29424. *Alternaria panax* spores can germinate profusely in under 24 hours, an initial stage in causing leaf and stem blight. During spore germination, germ tubes grow and find or make entry points into plant stems and leaves, beginning the process of infection. At germination, other Alternaria species have also been shown to release one or more deleterious toxic substances that promote infection. It is hypothesized that *Alternaria panax* does the same.

Inhibition of Alternaria spore germination may also occur on plant leaves and stems, leading to a reduction in disease. For example, ginseng seedlings inoculated with a biologically pure preparation of *Pseudomonas cepacia* cells are protected from infection by *Alternaria panax*, as shown in the following examples. Such inoculation may be conveniently made by spraying a suspension of cells through an artist's airbrush onto the leaflets until the leaflets are wet. While successful protection has been achieved using suspension cultures at approximately $10^8$ cells/ml, it is believed that cells at other concentrations would also be effective. Moreover, filtrates of *Pseudomonas cepacia* cultures which contain effective biocontrol agents produced by the cells, but not the cells themselves, also inhibit Alternaria spore germination.

The inoculant is preferably diluted with a suitable carrier or extender so as to make the inoculant easier to handle and to provide a sufficient quantity of material so as to be capable of easy human handling. Examples of suitable carriers include water, culture media, or saline solutions.

To further identify the bacterial strains AMMA and AMMD, a fatty acid profile for each was determined by mass spectrometric analysis.

With reference to FIG. 1, the results of the tests to determine the fatty acid profile for *Pseudomonas cepacia* AMMD are presented below in Table 1:

TABLE 1

| RT | Area | Ar/Ht | Respon | ECL | Name | % | Comment 1 | Comment 2 |
| --- | --- | --- | --- | --- | --- | --- | --- | --- |
| 1.613 | 40748000 | 0.081 | ... | 7.052 | SOLVENT PEAK | ... | <min rt | |
| 4.446 | 1993 | 0.031 | 1.036 | 12.000 | 12:0 | 1.00 | ECL deviates 0.000 | Ref −0.001 |
| 6.826 | 5489 | 0.038 | 0.969 | 14.000 | 14:0 | 2.59 | ECL deviates −0.000 | Ref −0.002 |
| 9.107 | 9988 | 0.042 | 0.944 | 15.493 | Sum In Feature 3 | 4.59 | ECL deviates 0.003 | 14:0 3OH/16:1 ISO |
| 9.634 | 30599 | 0.043 | 0.941 | 15.818 | 16:1 CIS 9 | 14.02 | ECL deviates 0.001 | |
| 9.928 | 36362 | 0.044 | 0.940 | 16.000 | 16:0 | 16.63 | ECL deviates 0.000 | Ref −0.002 |
| 10.083 | 1560 | 0.070 | ... | 16.092 | | ... | | |
| 11.436 | 16563 | 0.048 | 0.936 | 16.890 | 17:0 CLCLO | 7.55 | ECL deviates 0.002 | Ref 0.000 |
| 11.714 | 1747 | 0.046 | 0.936 | 17.052 | 16:1 2OH | 0.80 | ECL deviates 0.005 | |
| 12.034 | 1387 | 0.049 | 0.936 | 17.237 | 16:0 2OH | 0.63 | ECL deviates 0.002 | |

TABLE 1-continued

| | | | | | | | | |
|---|---|---|---|---|---|---|---|---|
| 12.532 | 11342 | 0.048 | 0.937 | 17.524 | 16:0 3OH | | 5.17 ECL deviates 0.004 | |
| 12.934 | 1066 | 0.044 | ... | 17.756 | | | ... | |
| 13.051 | 86323 | 0.047 | 0.937 | 17.823 | Sum In Feature 7 | | 39.38 ECL deviates 0.001 | 18:1 CIS 11/t 9/t 6 |
| 13.354 | 1722 | 0.047 | 0.938 | 17.998 | 18:0 | | 0.79 ECL deviates −0.002 | Ref −0.003 |
| 14.143 | 1445 | 0.067 | ... | 18.453 | | | ... | |
| 14.489 | 1051 | 0.057 | ... | 18.652 | | | ... | |
| 15.921 | 9636 | 0.048 | 0.943 | 18.901 | 19:0 CYCLO C11-12 | | 4.42 ECL deviates 0.001 | Ref 0.000 |
| 15.249 | 5288 | 0.057 | 0.945 | 19.091 | 18:1 2OH | | 2.43 ECL deviates 0.003 | |
| 17.137 | 1003 | 0.043 | ... | 20.191 | | | ... >max rt | |
| ****** | 9988 | ... | ... | ... | SUMMED FEATURE 3 | | 4.59 12:0 ALDE? | unknown 10.9 |
| ****** | ... | ... | ... | ... | | | ... 16:1 ISO I/14:0 3OH | 14:0 3OH/ 16:1 ISO I |
| ****** | 86323 | ... | ... | ... | SUMMED FEATURE 7 | | 39.38 18:1 CIS 11/t 9/t 6 | 18:1 TRANS 9/t6/c11 |
| ****** | ... | ... | ... | ... | | | ... 18:1 TRANS 6/t9/c11 | |

| Solvent Ar | Total Area | Named Area | % Named | Total Amnt | Nbr Ref | ECL Deviation | Ref ECL Shift |
|---|---|---|---|---|---|---|---|
| 748000 | 223561 | 218439 | 97.71 | 205479 | 6 | 0.002 | 0.002 |

TSBA [Rev 2.0]

| | |
|---|---|
| Pseudomonas | 0.591 |
| P. cepacia | 0.591 |
| P. c. cepacia GC subgroup B | 0.591 |

Comparison with TSBA [Rev 2.0]: Pseudomonas-cepacia-cepacia GC subgroup B-Distance: 3.04

```
              0    5   10   15   20   25   30   35   40   45   50   55   60   65   70   75
12:0              .*.
11:0 ISO 3OH   *-
13.1 AT 12-13  *-
14:0           -+x---
16:1 CIS 9             .-------*-+-------
16:1 C         *
16:0                        .-------x+-----
17:0 CYCLO     .-------+x---
17:0           *-
16:1 2OH      .*-
16:0 2OH      .*-
16:0 3OH       . -+x-
18:0          .*-
19:0 CYCLO    ---*--------
C11-12
18:1 2OH      --*--
SUMMED         . -*-
FEATURE 3
SUMMED                              ---+---x-
FEATURE 7
```

Figure 2:
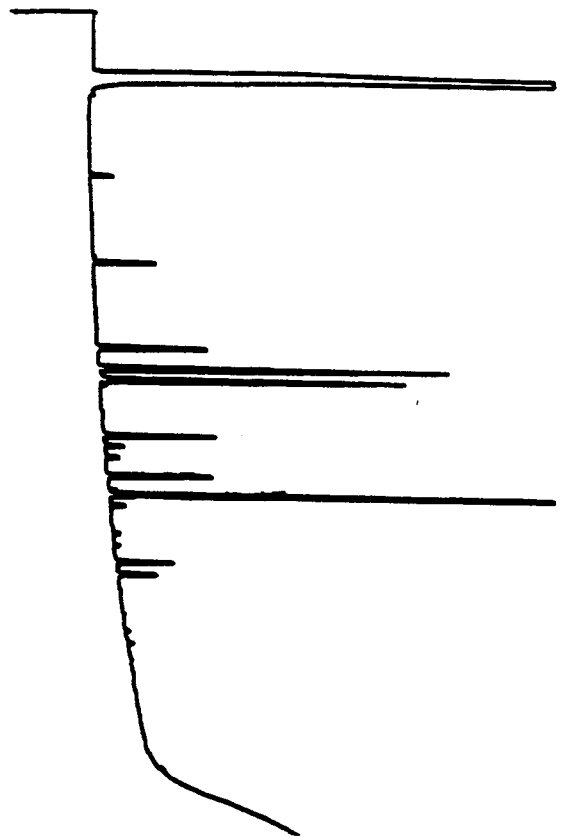
FIG. 2 is a graph illustrating the results of the mass spectrometric analysis of the fatty acid profile of *Pseudomonas cepacia* AMMA.

With reference to FIG. 2, the results of the tests to determine the fatty acid profile for *Pseudomonas cepacia* AMMA are presented below in Table 2:

TABLE 2

| RT | Area | Ar/Ht | Respon | ECL | Name | % | Comment 1 | Comment 2 |
|---|---|---|---|---|---|---|---|---|
| 1.613 | 40748000 | 0.081 | ... | 7.051 | SOLVENT PEAK | ... | <min rt | |
| 4.447 | 1548 | 0.036 | 1.036 | 12.000 | 12:0 | 0.98 | ECL deviates 0.000 | Ref 0.000 |
| 6.828 | 4415 | 0.038 | 0.969 | 14.000 | 14:0 | 2.63 | ECL deviates −0.000 | Ref −0.001 |
| 9.108 | 8547 | 0.042 | 0.944 | 15.493 | Sum In Feature 3 | 4.59 | ECL deviates 0.003 | 14:0 3OH/16:1 ISO I |
| 9.636 | 27640 | 0.042 | 0.941 | 15.819 | 16:1 CIS 9 | 15.97 | ECL deviates 0.002 | |
| 9.928 | 25281 | 0.044 | 0.940 | 15.999 | 16:0 | 14.58 | ECL deviates 0.001 | Ref −0.002 |
| 11.437 | 9844 | 0.047 | 0.936 | 16.890 | 17:0 CLCLO | 5.66 | ECL deviates 0.002 | Ref 0.000 |
| 11.714 | 1646 | 0.047 | 0.936 | 17.052 | 16:1 2OH | 0.95 | ECL deviates 0.005 | |
| 12.034 | 1188 | 0.047 | 0.936 | 17.236 | 16:0 2OH | 0.68 | ECL deviates 0.001 | |
| 12.534 | 9443 | 0.048 | 0.937 | 17.524 | 16:0 3OH | 5.43 | ECL deviates 0.004 | |
| 12.937 | 733 | 0.047 | ... | 17.757 | | ... | | |
| 13.053 | 73016 | 0.048 | 0.937 | 17.824 | Sum In Feature 7 | 42.01 | ECL deviates 0.001 | 18:1 TRANS 9/t6/c11 |
| 13.356 | 1307 | 0.046 | 0.938 | 17.998 | 18:0 | 0.75 | ECL deviates −0.002 | Ref −0.002 |
| 14.143 | 904 | 0.066 | ... | 18.452 | | ... | | |
| 14.922 | 5361 | 0.050 | 0.943 | 18.901 | 19:0 CYCLO C11-12 | 3.10 | ECL deviates 0.001 | Ref 0.001 |
| 15.251 | 3969 | 0.055 | 0.945 | 19.091 | 18:1 CYCLO C11-12 | 2.30 | ECL deviates 0.003 | |
| ****** | 8547 | ... | ... | ... | SUMMED FEATURE 3 | 4.95 | 12:0 ALDE? | unknown 10.928 |
| ****** | ... | ... | ... | ... | | ... | 16:1 ISO I/14:0 3OH | 14:0 3OH/ |

TABLE 2-continued

| | | | | | | 16:1 ISO I | | |
|---|---|---|---|---|---|---|---|---|
| ****** | 73016 | ... | ... | ... | SUMMED FEATURE 7 | 42.01 | 18:1 CIS 11/t 9/t 6 | 18:1 TRANS 9/t6/c11 |
| ****** | ... | ... | ... | ... | | | 18:1 TRANS 6/t9/c11 | |

| Solvent Ar | Total Area | Named Area | % Named | Total Amnt | Nbr Ref | ECL Deviation | Ref ECL Shift |
|---|---|---|---|---|---|---|---|
| 748000 | 174842 | 173205 | 99.06 | 162924 | 6 | 0.002 | 0.001 |

TSBA [Rev 2.0]

| | |
|---|---|
| Pseudomonas | 0.440 |
| P. cepacia | 0.440 |
| P. c. cepacia GC subgroup B | 0.440 |

Comparison with TSBA [Rev 2.0]: Pseudomonas-cepacia-cepacia GC subgroup B-Distance: 3.801

```
                0   5  10  15  20  25  30  35  40  45  50  55  60  65  70  75  80  85  90  95 100
12:0           .-*--     .   .   .   .   .   .   .   .   .   .   .   .   .   .   .   .   .   .
11:0 ISO 30H   *-    .   .   .   .   .   .   .   .   .   .   .   .   .   .   .   .   .   .   .
13.1 AT 12-13  *-    .   .   .   .   .   .   .   .   .   .   .   .   .   .   .   .   .   .   .
14:0           -+x---    .   .   .   .   .   .   .   .   .   .   .   .   .   .   .   .   .   .
16:1 CIS 9     .     .---------*---------   .   .   .   .   .   .   .   .   .   .   .   .   .
16:1 C         *     .   .   .   .   .   .   .   .   .   .   .   .   .   .   .   .   .   .   .
16:0           .     .   -x----*----      .   .   .   .   .   .   .   .   .   .   .   .   .   .
17:0 CYCLO     .------x+----     .   .   .   .   .   .   .   .   .   .   .   .   .   .   .   .
17:0           *-    .   .   .   .   .   .   .   .   .   .   .   .   .   .   .   .   .   .   .
16:1 20H       -*-   .   .   .   .   .   .   .   .   .   .   .   .   .   .   .   .   .   .   .
16:0 20H       -*-   .   .   .   .   .   .   .   .   .   .   .   .   .   .   .   .   .   .   .
16:0 30H       .  -+x-    .   .   .   .   .   .   .   .   .   .   .   .   .   .   .   .   .   .
18:0           -*-   .   .   .   .   .   .   .   .   .   .   .   .   .   .   .   .   .   .   .
19:0 CYCLO     -x+-----   .   .   .   .   .   .   .   .   .   .   .   .   .   .   .   .   .   .
C11-12
18:1 20H       --*--    .   .   .   .   .   .   .   .   .   .   .   .   .   .   .   .   .   .
SUMMED         .  -*-    .   .   .   .   .   .   .   .   .   .   .   .   .   .   .   .   .   .
FEATURE 3
SUMMED         .     .   .   .   .   .   ---*------x    .   .   .   .   .   .   .   .   .   .
FEATURE 7
```

The following non-limitative examples are designed to illustrate the present invention:

EXAMPLES

Example 1

Example 1 was conducted to isolate and determine particular bacterial strains which are effective biocontrol agents for the Aphanomyces fungi. Approximately 200 bacterial strains were isolated from pea roots grown in Wisconsin soils infested with Aphanomyces. Each isolate was grown in a nutrient broth (NBY) and coated onto a captan-treated pea seed (Perfection 8221). The term "captan" refers to a fungicide having the chemical name N-(Trichloromethylthio) tetrahydrophthalimide. The coated seeds were air-dried prior to planting.

The coated seeds and the control seeds were then planted in 60 cc. cone-shaped containers, as illustrated in FIG. 3, containing either pasteurized soil or naturally infested (with Aphanomyces) field soil. Unless otherwise defined, the control in each of the experiments was a captan-treated pea seed. The pasteurized soil was inoculated with $2 \times 10^4$ Aphanomyces zoospores six days after planting. The plants were then grown under greenhouse conditions for approximately three weeks, after which the disease symptoms and shoot dry weights were measured.

The following bacterial strains, listed in Table 3, were identified as the best strains in terms of improvement in shoot dry weights and decreased disease symptoms over control conditions:

TABLE 3

| Bacterial Strain | % Shoot Wt. Increase Compared to Control |
|---|---|
| CRK449 | 19.5 |
| 5A | 19.9 |
| CRK424 | 20.0 |
| AMMD | 20.2 |
| PRA44 | 20.2 |
| CRK419 | 20.6 |
| PRA25 | 21.2 |
| PRA42 | 22.6 |
| PRA48 | 23.0 |
| CRK468 | 25.1 |
| CRK478 | 27.7 |
| PRA15 | 45.2 |
| AMMA | 52.7 |

The bacterial strains which showed the greatest promise in reducing pea root rot and disease severity, as well as increasing shoot dry weight, were then tested under field conditions (Example 2). Strains listed above other than AMMA and AMMD are not considered further herein.

EXAMPLE 2

Example 2 was designed to test strain AMMD for biocontrol activity on pea seeds. The bacterial strain was cultured and coated onto pea seeds according to the methods described in Example 1. The seeds were then replica planted 5 times and were allowed to grow for one season (8 weeks).

Plant mortality was evaluated weekly and the plant yield in this experiment was determined using the dry weight of the pea plants measured. The results of this experiment are presented below in Table 4. It is to be noted that the disease was so prevalent in this experiment that no pea pods formed.

TABLE 4

| Bacterial Strain | Mean Shoot Dry Wt., g | % Difference** |
|---|---|---|
| control | 61 | — |
| AMMD | 94* | +55 |
| AMMA | 103* | +70 |

*P less than .05 Dunnett Test
**Between the treatments AMMD and the control.

Next, strain AMMD was tested in field trials conducted in locations representing a range of Aphanomyces densities. The methods and materials were conducted in a manner similar to the previous test. The plant mortality due to Aphanomyces was evaluated weekly. Plant yield was determined using the dry weight of the peas at dry seed stage. The results of this experiment are presented below in Table 5.

TABLE 5

| Bacterial Strain Difference | Mean Dry Wt. Peas, g | % Yield |
|---|---|---|
| control | 175 | — |
| AMMD | 282 | 61 |

From Table 5, it can be seen that the bacterial strain AMMD increased the average seed yield by 61%, compared to the non-coated controls.

In the final Aphanomyces experiment, performed under conditions similar to the previous experiments, although the yield here was determined using the fresh weight of peas. The results of this experiment can be found below in Table 6:

TABLE 6

| Bacterial Strain Difference | Mean Fresh Wt. Peas, g | % Yield |
|---|---|---|
| control | 105 | — |
| AMMD | 188 | 79 |

*Pseudomonas cepacia* strain AMMD increased yield by 79%

EXAMPLE 3

Example 3 was conducted to examine the in vitro effects of *Pseudomonas cepacia* strains on spore germination of Alternaria fungi.

*Alternaria panax* 1268 was allowed to germinate in the presence or absence of various *Pseudomonas cepacia* isolates having other biocontrol activity in plants, tabulated below.

Alternaria parent plates were produced on clarified V8 agar using refrigerated stock cultures. The parent plates were incubated in plastic culture boxes containing small beakers of distilled water at 20° C. for about four days. At that time, the cultures were transferred to fresh clarified V8 agar. Spores were obtained 13 or 14 days later by gently swirling 9–10 ml of sterile 0.01% Tween-80 per 9 cm plate and then pouring off the liquid into a small sterile beaker containing a stir bar. The spore suspension was stirred gently and spore concentration was determined by hemocytometer count. The concentration was adjusted with sterile distilled water to about 250–300 spores per 0.02 ml. Next, 0.02 ml of the suspension was distributed to each test well of microtiter plates. The density was checked in a few test wells to ensure accurate spore dispersion.

The various *Pseudomonas cepacia* bacterial isolates were prepared by plating frozen stock cultures onto TGE plates which were incubated at room temperature. After 2 days, the bacteria were transferred to fresh TGE plates. Three days later, a generous amount of bacteria was collected on sterile wire loops, placed into 100 ml of sterile 0.85% NaCl in a 250 ml sterile flask. To make a uniform suspension, the liquid in the flask was swirled, sonicated for 30 seconds and shaken.

To determine whether the *Pseudomonas cepacia* isolate could inhibit spore germination, 0.02 ml of the bacterial cell suspension was added to each spore-containing well. 0.85% NaCl and sterile distilled water were also tested as negative controls. Test and control microtiter plates were placed in the plastic culture box, as above, in a 20° C. growth chamber for about 24 hours, during which time germination was allowed to proceed. The spores were then fixed to the well bottoms by adding 0.01 ml of 4% glutaraldehyde to each well. The fixed microtiter plates were then refrigerated until scored.

To determine the extent of germination, 100 spores in each fixed well were classified as germinated or ungerminated when viewed under an inverted microscope. A spore was considered germinated if the length of the germ tube was equal to or greater than the width of the spore. Broken spores were not counted, nor were those in which clumping made it impossible to determine the germ tube origin.

Table 7 depicts three separate tests of the ability of *A. panax* spores to germinate in the presence of thirteen different *Pseudomonas cepacia* isolates known to have biocontrol activity which were obtained from various sources. Unless otherwise noted, the mean percentage of germination reflects an average score of 3 wells. Also presented, is the log CFU/ml, a measure of the number of bacterial cells added per well. While germination was reduced in one or two tests of each isolate, two isolates, AMMD and 29424 consistently demonstrated marked inhibition, virtually eliminating germination of *A. panax* spores.

TABLE 7

| | TRIAL 1 | | TRIAL 2 | | TRIAL 3 | |
|---|---|---|---|---|---|---|
| Isolate: | Mean % germination | log CFU/ml | Mean % germination | log CFU/ml | Mean % germination | log CFU/ml |
| 17759 | 96.33 | 7.63 | 24.33 | 7.30 | 0.67 | 7.68 |
| B14149 | 96.67 | 8.14 | 53.67 | 7.94 | 63.00 | 8.04 |
| 17616 | 96.00 | 8.60 | 87.00 | 8.23 | 69.00 | 8.11 |
| 29424 | 0.33 | 8.07 | 0.00 | 7.88 | 0.00 | 7.83 |
| 64-22K | 87.00 | 6.74 | 0.00 | 6.73 | 12.67 | 5.00* |
| 25416 | 97.67 | 7.69 | 69.67 | 7.55 | 21.67 | 7.59 |
| 10856 | 99.67 | 7.51 | 22.67 | 7.64 | 1.33 | 8.00 |
| 25610 | 91.33 | 8.17 | 51.67 | 7.90 | 55.33 | 7.81 |
| 17765 | 93.67 | 8.30 | 70.67 | 8.14 | 67.00 | 7.90 |
| 17460 | 97.33 | 7.39 | 80.33 | 6.86 | 81.00 | 6.90 |
| RJ2 | 94.33 | 6.82 | 0.00 | 6.90 | 26.00 | 6.53 |
| OK-1 | 51.67 | 8.07 | 1.00 | 7.60 | 43.67 | 7.63 |
| AMD | 0.00 | 8.23 | 0.33 | 7.92 | 0.00 | 7.91 |
| sd$H_2O$ | 59.33 | | 63.33 | | 70.33 | |
| 0.85% NaCl | 93.00 | | 96.67 | | 89.00 | |

*Two colonies at $10^{-4}$ dilution.

EXAMPLE 4

Example 4 was conducted to determine whether cell-free filtrates of several *Pseudomonas cepacia* isolates would also inhibit spore germination of *Alternaria panax* and other Alternaria species. Bacterial suspensions were prepared as in Example 3. To prepare cell-free filtrates of the bacterial suspensions, 6–7 ml of each suspension was centrifuged for 10 minutes to pellet the cells. The supernatant (5 ml) was removed with a sterile needle and syringe and filtered through a 0.2μ Acrodisc filter.

The filtrate (0.02 ml) was employed in place of bacterial suspensions in microtiter well germination assays like those of the previous example. To ensure that the filtrate was cell-free, 100 μl of each filtrate was also plated onto each of several TGE plates on which colonies would have formed had cells been present.

Seven *Pseudomonas cepacia* isolates and filtrates of each isolate prepared as described above, were tested for the ability to inhibit *A. panax* spore germination. Table 8 demonstrates that all except 17616 are able to reduce or prevent *A. panax* spore germination, suggesting that many *Pseudomonas cepacia* isolates may be employed to prevent the leaf and stem blight caused by Alternaria in foliar plants within the method of the present invention. In particular the well-characterized and ATCC-deposited strains AMMA and AMMD are effective inhibitors of *A. panax*. Furthermore, these data demonstrate that the germination-inhibiting or disease-reducing factor can be effective even when the cells producing the factor have been removed.

TABLE 8

| Treatment A. panax spores plus: | TRIAL 1 Mean % germination | TRIAL 2 Mean % germination | TRIAL 3 Mean % germination | TRIAL 4 Mean % germination |
| --- | --- | --- | --- | --- |
| Pc 22 cells | 0.33 | 0.00 | 0.00 | |
| Pc 22 filtrate | | 0.00 | 2.67 | 11.33 |
| Pc 32 cells | 0.00 | 0.00 | 0.00 | |
| Pc 32 filtrate | | 1.33 | 0.33 | 7.00 |
| Pc 742 cells | 0.33 | 0.00 | 0.00 | |
| Pc 742 filtrate | | 0.00 | 0.00 | 16.00 |
| LT-4-12W cells | 0.67 | 0.00 | 0.00 | |
| LT-4-12W filtrate | | 0.67 | 0.00 | 8.00 |
| AMMA cells | 0.67 | 0.00 | 0.00 | |
| AMMA filtrate | | 0.00 | 0.00 | 11.33 |
| AMMD cells | 24.33 | 0.00 | 0.00 | |
| AMMD filtrate | | 0.33 | 0.00 | 14.33 |
| 17616 cells | | 98.00 | 99.33 | |
| 17616 filtrate | | 98.67 | 100.00 | |
| 0.85% NaCl | | 99.33 | 98.33 | 97.33 |
| sdH$_2$O | 93.00 | 98.67 | 97.67 | 99.00 |

Similar spore germination assays presented below in Tables 9 and 10 allowed *Alternaria brassicicola* and *Alternaria solani* spores, respectively, to germinate in the presence or absence of AMMD cells or the filtrate of AMMD cells. *A. brassicicola* is a foliar pathogen of crucifers. *A. solani* causes early blight of potato. These two tables demonstrate the effectiveness of *Pseudomonas cepacia* cells and cell filtrates, particularly strain AMMD, in inhibiting spore germination in Alternaria species other than *A. panax*. Moreover, biocontrol by these strains against several Alternaria species suggests effective inhibition of infections caused by other Alternaria strains in the field.

TABLE 9

| A. brassicicola plus | TRIAL 1 Mean % germination | S.d. | TRIAL 2 Mean % germination | S.d. | TRIAL 3 Mean % germination | S.d. |
| --- | --- | --- | --- | --- | --- | --- |
| AMMD cells | 0 | 0.000 | 0.2 | 0.447 | 0.2 | 0.447 |
| AMMD filtrate | 0 | 0.000 | 0.2 | 0.445 | 0.0 | 0.000 |
| 0.85% NaCl | 90 | 3.082 | 93.8 | 2.280 | 94.6 | 3.782 |

TABLE 9-continued

| A. brassicicola plus | TRIAL 1 Mean % germination | S.d. | TRIAL 2 Mean % germination | S.d. | TRIAL 3 Mean % germination | S.d. |
| --- | --- | --- | --- | --- | --- | --- |
| sdH$_2$O | 81 | 6.042 | 94.6 | 3.507 | 97.0 | 3.391 |

Note:
Percent germination is the average of five wells.

TABLE 10

| A. solani spores from isolate: | Treatment | TRIAL 1 Mean % germ | TRIAL 2 Mean % germ | TRIAL 3 Mean % germ |
| --- | --- | --- | --- | --- |
| 91-8 | AMMD cells | 0.67 | 0.00 | 0.33 |
| 91-8 | AMMD filtrate | 6.33 | 0.00 | 0.00 |
| 91-8 | 0.85% NaCl | 96.67 | 85.00 | 72.67 |
| 91-8 | sdH$_2$O | 99.33 | 71.67 | 67.67 |
| 2 | AMMD cells | 0.00 | 0.00 | 0.67 |
| 2 | AMMD filtrate | 0.67 | 0.33 | 0.67 |
| 2 | 0.85% NaCl | 96.00 | 86.67 | 37.67 |
| 2 | sdH$_2$O | 99.67 | 73.00 | 62.00 |
| 3 | AMMD cells | 0.00 | | |
| 3 | AMMD filtrate | 0.00 | | |
| 3 | 0.85% NaCl | 76.67 | | |
| 3 | SdH$_2$O | 99.00 | | |

EXAMPLE 5

Example 5 was conducted to determine whether *Pseudomonas cepacia* cells and cell-free filtrates could protect ginseng seedlings from *A. panax*-caused leaf and stem blight in vivo. Spores from *A. panax* strain 1268 were prepared as described in Example 3, except that spores used to inoculate ginseng seedlings were diluted to approximately 5×10$^3$ spores per ml in sterile distilled water.

*Pseudomonas cepacia* strained AMMD bacteria were prepared from TGE plates by scraping 5 plates of bacteria into 0.85% NaCl solution using a rubber policeman. As in the previous examples, the suspension was shaken and sonicated to evenly distribute the bacteria. Until inoculation, the cell suspension was stored at −10° C. To prepare a cell-free filtrate, an aliquot of the suspension was removed to sterile centrifuge tubes and was spun for about 25–30 minutes at 15,000 rpm. The supernatant was removed and passed through a 0.45μAcrodisc filter. The filtrate was frozen at −80° C., thawed and refrozen twice, and stored until use. On inoculation day, the filtrate was thawed for a third time.

To simulate Alternaria infection of ginseng seedlings and to monitor the effect of *Pseudomonas cepacia* AMMD on spore germination, four week old ginseng seedlings transplanted into conical containers were inoculated with *A. panax* spores and *Pseudomonas cepacia* cell suspensions or cell-free filtrates.

Inoculation was performed using an artist's airbrush attached to a forced air outlet. To clean the airbrush, the fluid path was purged with 95% ethanol and then with sterile distilled water. The air pressure was adjusted to the lowest that gave a strong spray without blasting the leaves. The aperture of the airbrush was adjusted to the smallest opening that allowed a wet spray to leave droplets on the leaves. The seedlings were sprayed by inverting each cone so that the top side of the leaf rested on paper towels and by spraying the undersides of the leaflets until liquid ran off the leaves. This procedure was used to apply both *A. panax* spores and *Pseudomonas Cepacia* cell suspensions and cell-free extracts. Spores were usually added last though in some experiments, spores were added first. Between each application, ethanol and sterile distilled water were forced through the liquid path of the airbrush.

After inoculation, racks of cones were placed in a 20° C. dew chamber for about 24 hours. The racks were then removed and placed in a growth chamber. The seedlings were observed for lesion development and each leaflet was rated on a scale of 0 to 4 (0=healthy leaflet; 4=dead leaflet) between 3 and 10 days after inoculation (dai). Tables 11-15, which present Bonferroni-corrected time course data, summarize the mean leaf disease rating of seedlings treated as described. Tables 11 and 12 summarize biocontrol of *A. panax* spore germination by D cells. Tables 13-15 directly compare the biocontrol of *A. panax* by *Pseudomonas cepacia* AMMD cells and filtrate in separate trials. The leaf disease rating reflects the sum of the 0-4 rating of each ginseng seedling leaflet. Accordingly, therefore, the maximum possible disease leaf rating of a 3-leaflet ginseng seedling is 12.

The data of these tables demonstrate that both *Pseudomonas cepacia* AMMD cells and filtrates protect ginseng seedlings from leaf blight caused by *Alternaria panax*. Although both cells and filtrate appear to have protective ability, the cells performed consistently better than the filtrate. The protective activity of the filtrate was greatest during approximately the first week after inoculation.

TABLE 11

| | Mean leaf disease rating | | | | | | |
|---|---|---|---|---|---|---|---|
| Treatment | 3 dai | 5 dai | 6 dai | 7 dai | 8 dai | 9 dai | 10 dai |
| P.c. cells | 0.0000 | 0.0000 | 0.0000 | 0.0000 | 0.0000 | 0.0000 | 0.0000 |
| 0.85% NaCl | 0.0000 | 0.0000 | 0.0000 | 0.0000 | 0.0000 | 0.0000 | 0.0000 |
| A.p. spores | 2.1063 | 8.7937 | 9.8125 | 10.7000 | 11.1250 | 11.2500 | 11.5250 |
| P.c. cells + A.p. spores | 0.2500 | 1.1090 | 1.5705 | 1.7756 | 1.9295 | 1.8782 | 2.0066 |
| P.c. cells + 0.85% NaCl + A.p. spores | 0.1841 | 0.3685 | 0.7894 | 1.1053 | 1.1053 | 1.1053 | 1.2105 |

TABLE 12

| | Mean leaf disease rating | | | | | | |
|---|---|---|---|---|---|---|---|
| Treatment | 3 dai | 5 dai | 6 dai | 7 dai | 8 dai | 9 dai | 10 dai |
| P.c. cells | 0.0000a | 0.0000a | 0.000a | 0.000a | 0.000a | 0.000a | 0.000a |
| 0.85% NaCl | 0.0000a | 0.0000a | 0.000a | 0.000a | 0.000a | 0.000ab | 0.000a |
| P.c. cells + A.p. spores | 0.1250a | 0.5000a | 0.750a | 0.917a | 1.000a | 1.042b | 1.042b |
| 085% NaCl + A.p. spores | 3.5833b | 8.3333b | 10.833b | 11.208b | 11.417b | 11.792c | 11.875c |
| A.p. spores | 5.1364c | 9.4091b | 11.545b | 11.636b | 11.909b | 12.000c | 12.000c |

TABLE 13

| | Mean leaf disease rating | | | | | | |
|---|---|---|---|---|---|---|---|
| Treatment | 3 dai | 5 dai | 6 dai | 7 dai | 8 dai | 9 dai | 10 dai |
| P.c. cells + A.p. spores | 0.4722a | 1.2222a | 3.972a | 4.657a | 4.743a | 4.886a | 5.343a |
| P.c. filtrate A.p. spores | 1.5556b | 3.8056b | 7.694b | 8.611b | 9.500b | 9.917b | 10.111b |
| 0.85% NaCl + A.p. spores | 4.0556c | 8.3611c | 11.639c | 12.000c | 12.000c | 12.000c | 12.000b |

TABLE 14

| | Mean leaf disease rating | | | | | | |
|---|---|---|---|---|---|---|---|
| Treatment | 3 dai | 5 dai | 6 dai | 7 dai | 8 dai | 9 dai | 10 dai |
| P.c. cells + A.p. spores | 0.0000a | 0.0909a | 0.7273a | 0.818a | 0.864a | 0.955a | 1.091a |
| P.c. filtrate + A.p. spores | 0.7200b | 1.2800a | 3.8400b | 4.960b | 5.280b | 5.720b | 6.200b |
| 0.85% NaCl + A.p. spores | 2.4800c | 7.0800b | 9.4800c | 10.040c | 10.560c | 11.000c | 11.080c |

TABLE 15

| | Mean leaf disease rating | | | | | | |
|---|---|---|---|---|---|---|---|
| Treatment | 3 dai | 5 dai | 6 dai | 7 dai | 8 dai | 9 dai | 10 dai |
| P.c. cells + A.p. spores | 0.6207a | 2.321a | 3.143a | 3.607a | 3.893a | 4.964a | 5.750a |
| P.c. filtrate + A.p. spores | 2.1724b | 7.704b | 9.037b | 9.593b | 10.111b | 10.519b | 10.926b |
| 0.85% NaCl + | 3.7857c | 10.214c | 11.464c | 11.571b | 11.964b | 12.000b | 12.000b |

TABLE 15-continued

| Treatment | Mean leaf disease rating 3 dai | 5 dai | 6 dai | 7 dai | 8 dai | 9 dai | 10 dai |
|---|---|---|---|---|---|---|---|
| A.p. spores | | | | | | | |

It is understood that the invention is not confined to the particular construction and arrangement herein illustrated and described, but embraces such modified forms thereof as come within the scope of the following claims.

We claim:

1. A process for controlling Alternaria fungal foliar diseases in plants comprising inoculating the plants with an Alternaria disease-controlling effective amount of an essentially biologically pure culture of a *Pseudomonas cepacia* bacterial strain in which in an in vitro assay inhibits Alternaria spore germination, the *Pseudomonas cepacia* bacterial strain being selected from the group consisting of strains AMMD (ATCC Accession No. 53795), AMMA (ATCC Accession No. 53796) and ATCC Accession No. 29424.

2. The process of claim 1 wherein the plants are ginseng plants.

3. The process of claim 1 wherein the Alternaria fungal diseases are caused by a fungus selected from the group consisting of *A. panax, A. brassicola,* and *A. solani.*

4. A process of controlling Alternaria fungal foliar diseases in plants comprising inoculating the plants with an Alternaria disease-controlling effective amount of a cell-free filtrate prepared from an essentially biologically pure culture of a *Pseudomonas cepacia* bacterial strain which in an in vitro assay inhibits Alternaria spore germination, the *Pseudomonas cepacia* bacterial strain being selected from the group consisting of strains AMMD (ATCC Accession No. 53795), AMMA (ATCC Accession No. 53796) and ATCC Accession No. 29424.

5. The process of claim 4 wherein the plants are ginseng plants.

6. The process of claim 4 wherein the Alternaria fungal diseases are caused by a fungus selected from the group consisting of *A. panax, A. brassicola,* and *A. solani.*

7. The process of claim 4 wherein the cell-free filtrate is prepared by dispersing the bacterial cells, pelleting the bacterial cells and filtering the supernatant to remove any remaining cells.

* * * * *